(12) United States Patent
Parrill-Baker et al.

(10) Patent No.: US 8,268,891 B1
(45) Date of Patent: Sep. 18, 2012

(54) AUTOTAXIN INHIBITORS

(75) Inventors: Abby Louise Parrill-Baker, Memphis, TN (US); Daniel Lee Baker, Memphis, TN (US)

(73) Assignee: University of Memphis Research Foundation, Memphis, TN (US)

( * ) Notice: Subject to any disclaimer, the term of this patent is extended or adjusted under 35 U.S.C. 154(b) by 661 days.

(21) Appl. No.: 12/270,840

(22) Filed: Nov. 13, 2008

Related U.S. Application Data

(60) Provisional application No. 61/002,687, filed on Nov. 13, 2007.

(51) Int. Cl.
*A61K 31/17* (2006.01)
*A61K 31/19* (2006.01)
*A61K 31/496* (2006.01)

(52) U.S. Cl. ........ 514/580; 514/279; 514/284; 514/339; 514/354; 514/585; 514/656; 514/755

(58) Field of Classification Search .................. 514/183, 514/580, 279, 284, 339, 354, 585, 656, 755
See application file for complete search history.

(56) References Cited

PUBLICATIONS

Parrill, "Virtual screening approaches for the identification of non-lipid autotaxin inhibitors", Bioorganic & Medicinal Chemistry (2008), 16(4), pp. 1784-1795.*
Hoeglund, "Characterization of non-lipid autotaxin inhibitors", Bioorganic & Medicinal Chemistry (2010), 18(2), pp. 769-776.*

* cited by examiner

*Primary Examiner* — Sreeni Padmanabhan
*Assistant Examiner* — Sahar Javanmard
(74) *Attorney, Agent, or Firm* — Wyatt, Tarrant & Combs, LLP; William S. Parks

(57) ABSTRACT

Classes of compounds that exhibit effective inhibition of autotaxin enzymes are provided. Such classes include thioureas, diphenyldiazerenes, xanthenes, and isoindoles and exhibit reactivity with autotaxin to ultimately reduce the size of the reactive sites thereon to prevent conversion of lysophosphatidyl choline to lysophophatidic acid. Furthermore, such compounds can be incorporated within delivery forms for human ingestion. As such, these compounds accord an excellent manner of potentially reducing generation of certain cancers attributable to the presence of naturally occurring autotaxin within the human body. Methods of inactivating autotaxin to certain degrees therewith such compounds are encompassed within invention as well.

4 Claims, No Drawings

AUTOTAXIN INHIBITORS

CROSS-REFERENCE TO RELATED APPLICATIONS

This application claims priority of and is thus a conversion from provisional application 61/002,687, filed on Nov. 13, 2007.

FIELD OF THE INVENTION

Classes of compounds that exhibit effective inhibition of autotaxin enzymes are provided. Such classes include thioureas, diphenyldiazerenes, xanthenes, and isoindoles and exhibit reactivity with autotaxin to ultimately reduce the size of the reactive sites thereon to prevent conversion of lysophosphatidyl choline to lysophophatidic acid. Furthermore, such compounds can be incorporated within delivery forms for human ingestion. As such, these compounds accord an excellent manner of potentially reducing generation of certain cancers attributable to the presence of naturally occurring autotaxin within the human body. Methods of inactivating autotaxin to certain degrees therewith such compounds are encompassed within invention as well.

BACKGROUND OF THE PRIOR ART

All U.S. patents cited within this specification are hereby incorporated by reference.

Autotaxin, also known as ATX, ENPP2 or NPP2, short for Ectonucleotide pyrophosphatase phosphodiesterase 2 is an enzyme secreted within the human body. This molecule has been known for generating (LPA) through conversion of lysophosphatidyl-choline (LPC) thereto via lysophospholipase D activity (the removal of choline from the base compound generates LPA). LPA has been realized to contribute to tumor cell growth, unfortunately, as the reactivity within the human body of LPA within certain tissues has resulted, in certain studies, of cancerous growths when present at certain levels. In this manner, then, it has been theorized that the greater the incidence of autotaxin activity within the human body, the greater the possibility of LPA generation. A reduction in the catalytic capabilities of autotaxin to convert the LPC molecule to LPA would theoretically permit an ultimate reduction in possibility of unwanted cell proliferation through reduced LPA presence within a subject's body.

The mechanism of autotaxin in terms of enzymatic activity and catalysis to form LPA resides in its phosphodiesterase capability. LPA can be generated from the cleavage of the phophodiester bonds of LPC, as well as its function as a phospholipase enzyme (note Formula I).

Formula I

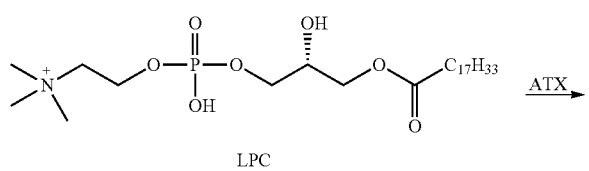

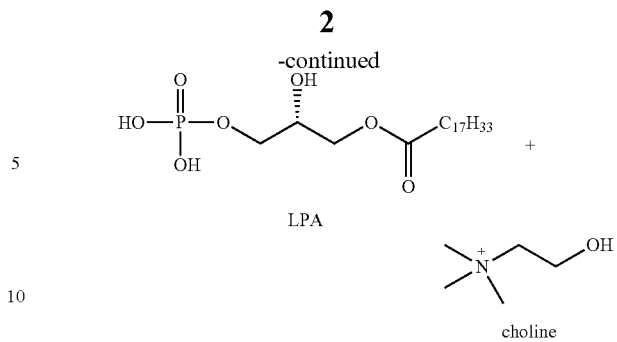

In extracellular fluids, this enzymatic catalysis of LPC removes the choline group, leaving LPA, which has a tendency to stimulate cell growth and proliferation as well as chemotaxis. From this, it appears that the motility of tumor cells is increased as well, resulting in properties and gene expression within certain carcinomas (such as, for instance, breast cancer cells), causing further processing into a form that is bioactive and potentially dangerous. Metastasis and oncogenesis of cancer cells appear to occur as well with elevated levels of LPA present within a targeted region. Increased ATX expression has been identified in renal carcinoma, metastatic breast cancer, thyroid carcinoma, Hodgkin lymphoma, and invasive glioblastoma multiforme.

It has thus been determined that the ability to prevent, or at least reduce, the amount of LPA within human body holds great promise at, likewise, reducing, if not preventing, the onset of certain cancers. It has been theorized, as noted above, that autotaxin modifications may prevent the undesirable conversion from LPC to LPA; the ability to actually accomplish such a result has been elusive, however, at least to the degree necessary for effective broad-scale utilization of such a method. Any modification thereof must exhibit an ability to drastically reduce the activity of autotaxin while also, preferably exhibiting oral bioavailability as well.

Past work at ATX inhibition has included L-histidine. Unfortunately, millimolar concentrations were required for any efficacy, and, more importantly, zinc sulfate presence (in submillimolar concentrations) suggested an inhibition mechanism involving interaction with the two native active site metal ions thereof. Other potential ATX inhibitors have included the products of ATX-catalyzed hydrolysis of LPC and sphingosyl phosphorylcholine (SPC), LPA, and S1P, respectively. Inhibition of ATX by LPA and S1P suggests that product feedback inhibition may contribute to regulation of ATX function in vivo. Previously reported ATX inhibitors share several common structural features, including a phosphate, thiophosphate, or phosphonate headgroup attached either with or without a linker to an alkyl chain, which can vary in overall length and can be either saturated or unsaturated. However, these compounds both lack substantial structural diversity and fail to meet Lipinski's empirical rules that characterize 90% of orally bioavailable drugs. It is of great importance to identify novel non-lipid structural classes capable of inhibiting ATX and which are orally bioavailable to treat certain tumor classes.

It is believed, without relying upon any specific scientific basis, that the lack of diversity in reported ATX inhibitors, as noted above, is due, in part, to the lack of a characterized three-dimensional structure of the enzyme. The ATX sequence of over 860 amino acids is divided into several domains, including a central catalytic domain composed of about 400 amino acids. ATX is a member of the nucleotide pyrophosphatase/phosphodiesterase (NPP) family, as well as the alkaline phosphatase superfamily. Crystallographic structures of several alkaline phosphatase superfamily members have been available for decades. These crystal structures show remarkable structural conservation in a small core surrounding the catalytic site, but unfortunately show completely different structural characteristics outside this conserved core. Sequence homology of the alkaline phosphatases with ATX does not exceed 14% and is therefore insufficient for generation of a high quality homology model in any region outside the approximately 100 amino acid structurally conserved core. The recent report of a crystal structure of a bacterial NPP enzyme with 30% identity to the ATX catalytic core domain enabled the development of a structural model of the ATX catalytic domain that may prove useful in structure-based drug design. Although a significant improvement, such a homology model must be applied cautiously as involvement of the c-terminal nuclease-like domain in substrate recognition has been suggested from studies of NPP family domain-swapping chimeras. In any event, these previously reported ATX inhibitors are analogs of LPA, a phospholipid, and are more hydrophobic than is typical of orally bioavailable drugs, thereby creating problems in that area.

As such, there exists a definitive lack in providing effective ATX inhibition (or inactivation) within the current knowledge base in this area, particularly as it concerns compounds that not only exhibit ATX inhibition, but also meet certain oral bioavailability requirements (as measured by Lipinski's rules). No such need has been met until now.

ADVANTAGES AND BRIEF DESCRIPTION OF THE INVENTION

It is thus an advantage of the present invention to provide reliable autotaxin inactivators for the purpose of reducing the conversion of LPC to LPA through the utilization of a readily available and easily produced compound (or compounds) that does not pose any significant health risks and exhibit the necessary oral bioavailability requirements. Another advantage is the ability for treatment with such compounds for cancer prevention treatment regimens.

Accordingly, this invention encompasses a method for treating cancerous tumors through the ingestion by a target patient exhibiting a cancerous tumor of at least one compound selected from the group consisting of at least one thiourea, at least one diphenyldiazerene, at least one xanthene, at least one isoindole, and any mixtures thereof. In particular, the compounds are selected from the group consisting of at least one of the following:

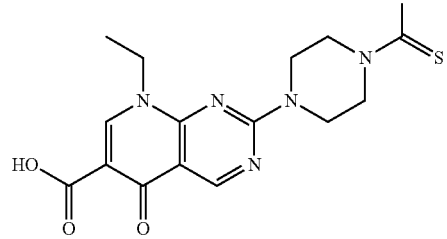
7839888

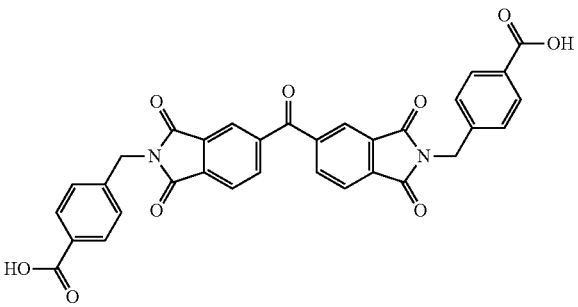
5761473

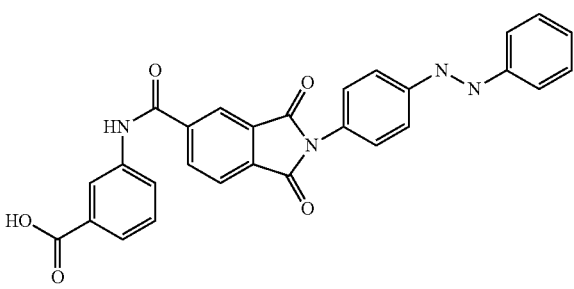
5564949

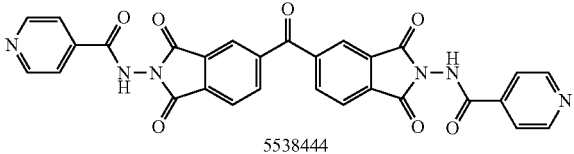
5538444

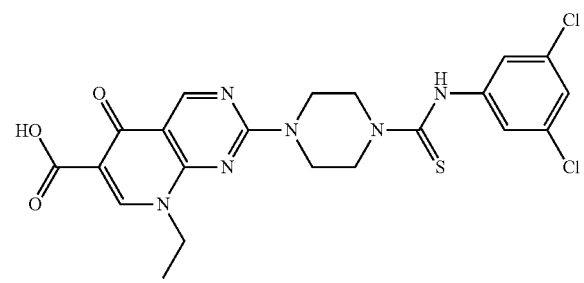
7905958

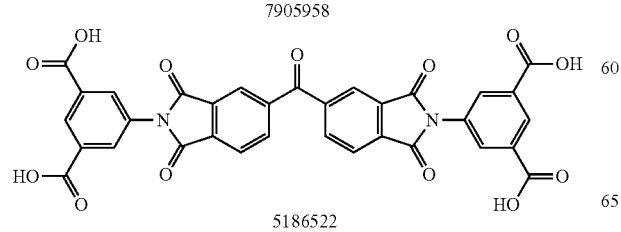
5186522

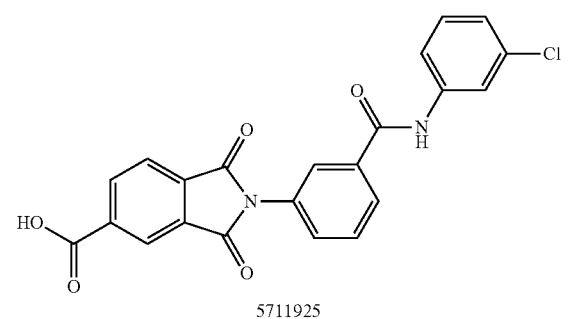
5711925

-continued

7921385

5210574

These compounds noted above exhibit a reduction in ATX-catalyzed FS-3 hydrolysis of target tumor cells by 50% or more at a concentration of about 10 µM. Such a reduction in activity of autotaxin is basically in terms of potential conversion of LPC to LPA, particularly through structural modifications to prevent placement of the LPC compound into the active site of the modified autotaxin enzyme.

DETAILED DESCRIPTION OF THE INVENTION AND PREFERRED EMBODIMENTS

The determination of proper ATX inhibition compounds was based upon the realization of certain structural requirements for proper reactivity with the ATX compound itself. Extensive review of possible compounds was undertaken through computer modeling of similarly structured compounds to the types noted above that exhibited ATX inhibition, but did not pass oral bioavailability test protocols. It was determined, for instance, that certain types of backbone compounds were effective, generally, and in theory for ATX inhibition. However, closer scrutiny was needed to effectively analyze the actual capability of each type of compound.

In essence, it was determined through a model of the ATX catalytic domain, residues 162-539 from the sequence of human ATX, developed by homology to Xac NPP, that certain basic configurations of ATX inhibitors were most likely necessary. Within this model, it was noted that all but 4 (1%) of the 317 non-proline and non-glycine residues occupy regions of Ramachandran space categorized as core secondary structures (232 residues, 73%), allowed regions (75 residues, 24%) or generously allowed regions (6 residues, 2%). (This model was, again, used in docking studies with two LPC species, 12:0 and 14:0, shown previously to be optimal ATX substrates.) Unrestrained docking studies failed to identify a pose placing the phosphorous atom of either substrate within a reasonable distance of T210, the catalytic residue responsible for initiating hydrolysis by forming a covalent bond to the phosphorous atom. This result was consistent with the report that substrate recognition elements reside outside the catalytic domain. Poses consistent with the role of LPC as an ATX substrate were identified when an anionic atom was required to occur within a 3.6 Å sphere centered 4.6 Å from both metal ions and 2.8 Å from the oxygen atom of T210. The phosphorous atom still preferred a location 6-7 Å from the oxygen atom of T210.

In greater detail, a model of human ATX was developed by homology to the Xac nucleotide pyrophosphatase/phosphodiesterase (NPP) crystal structure (entry 2GSU[31] in the Protein Data Bank). The sequence of human ATX (GenBank entry Q13822) was aligned with the sequence of Xac NPP using MOE and amino acids 1-161 and 540-863 of ATX were deleted as they did not correspond to amino acids contained in the Xac NPP structure. The ATX model was then generated by the homology model function in MOE, and divalent metal cations were transferred to corresponding locations in ATX from the Xac NPP crystal structure. Ionization states of histidine residues near divalent metal cations were adjusted to zero charge, with the deprotonated imidazole nitrogen nearest the cation. The ionization state of T210 was adjusted to −1, consistent with the pH profile demonstrated for Xac NPP.

Complexes of ATX with small molecules including substrates, inhibitors, and candidate inhibitors, were generated by docking using MOE. Each small molecule structure was constructed in the ionization state expected at pH 7. Functional groups with pKa values near seven, such as phosphate monoesters, were deprotonated due to the expected anionic stabilization provided by the active site metal ions. Residues with atoms within 6.5 Å of the active site metal ions were defined as the placement site. Small molecules were placed into ATX using the alphaPMI placement method, which matches the small molecule principle moments of inertia to alpha spheres distributed in closely packed locations within the docking site. Small molecule poses were scored using the affinityDG function, which approximates the enthalpic contribution to binding free energy. This combination of placement and scoring methods was selected based on comparison of results on two test systems. The alphaPMI placement and affinityDG energy function were found to reproduce the crystallographic position of rosiglitazone in PPARγ as well as our previous docked position of sphingosine 1-phosphate (S1P) within the validated model of the $S1P_1$ receptor. Docking simulations of small molecules with long alkyl chains additionally were performed multiple times due to the stochastic nature of the conformational sampling procedure and included an increased number of samples per conformation (50) and an increased number of poses (500) to improve sampling. Conformations for these highly flexible molecules were also precomputed in the absence of the receptor using the stochastic conformational search algorithm and all resulting conformations were rigidly docked into the receptor. Substrate docking studies were performed in the presence and absence of a restraint requiring an anionic atom to occur inside a 3.6 Å sphere centered 4.6 Å from both metal ions and 2.8 Å from the oxygen atom of T210. In all cases, the pose with the lowest score after elimination of ligand poses with strained conformations was selected for analysis and discussion.

This ATX catalytic domain homology model was, again, thus used as a docking target to identify promising candidate inhibitors for experimental screening. Initial analysis focused on anionic groups such as phosphate, sulfate, and carboxylate as well as bioisosteres of these anionic groups including phosphonamide, sulfonamide, and oxocarboxylate. Compounds showing better than 50% ATX inhibition at 10 µM by enzyme activity assay were used as similarity targets in subsequent analyses. Ninety-five structures were selected for screening out of 500 compounds docked against the ATX catalytic domain homology model. It was demonstrated that 19 of the 95 structures inhibited 20% or more of the ATX-catalyzed FS-3 hydrolysis at 10 µM concentration. This selection process was therefore 20% accurate in selecting compounds with some degree of ATX inhibition.

Docking studies with the ATX catalytic domain homology model were able to provide insight into activity differences of very similar structures. Very surprising results were noted, for example, with two different isoindole compounds that differed by the location of a carboxyl pendant group:

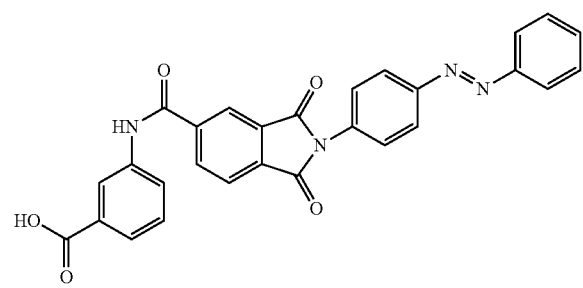

5564949

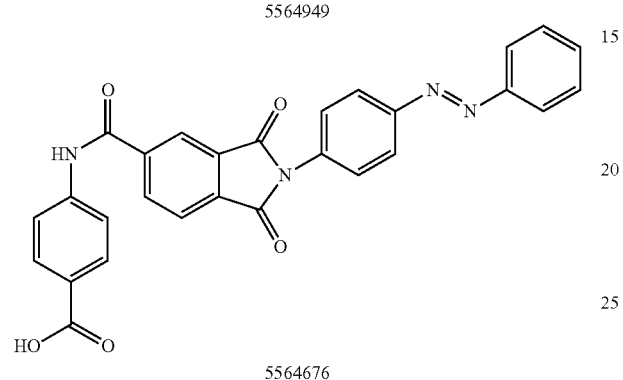

5564676

The 5564949 compound exhibited a 51% reduction in ATX inhibition at 10 micromole concentration, whereas the 5564676 compound showed no reduction levels at all (at the same concentration). Thus, selectivity between certain compounds, sometimes constitutional isomers even, was of necessity to determine effective ATX inhibitors. The 5564949 compound actually was found to display a number of favorable interactions in the docked complex in terms of ATX reactivity. These interactions include a cation-π interaction between the carboxylate functional group and 8284, an ion-pairing interaction between the carboxylate functional group and R285, and metal ligating interactions with the isoindole and diazerine functional groups. In contrast, the 5564676 failed to dock into the ATX catalytic domain model, suggesting that insufficient space was available for this molecule. Relocation of the carboxylate group of the 5564949 compound from the meta to the para position suggests that a very close, energetically unfavorable interaction would occur with the backbone of R284. These models are consistent with the difference in the ability of the 5564949 compound (meta isomer) and the 5564676 compound (para isomer) to inhibit ATX.

The full breadth of the specific compounds that met the ATX inhibition requirements through this modeling process and further analysis were:

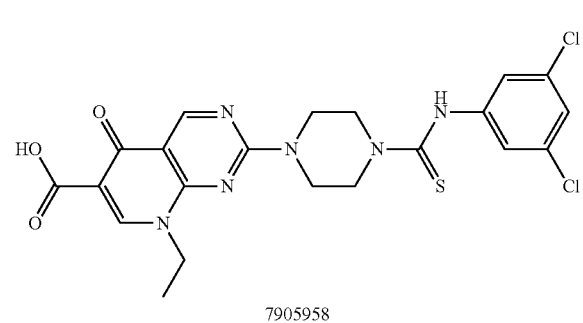

7905958

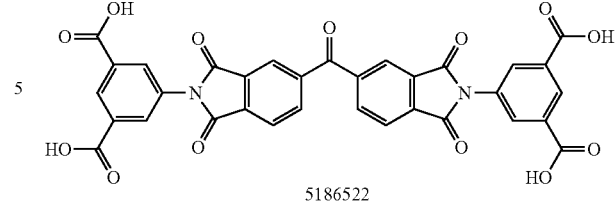

5186522

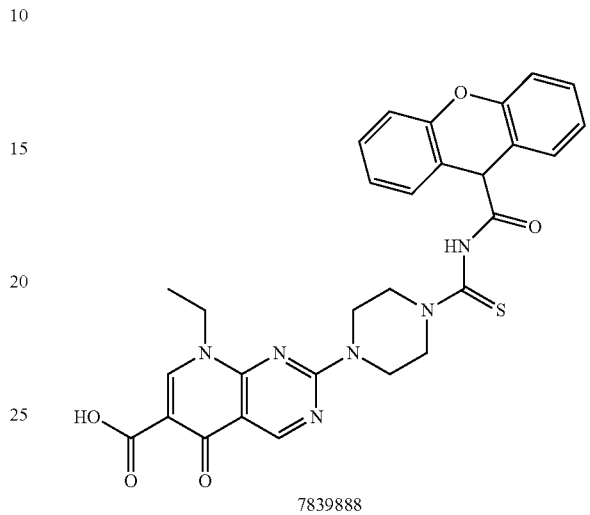

7839888

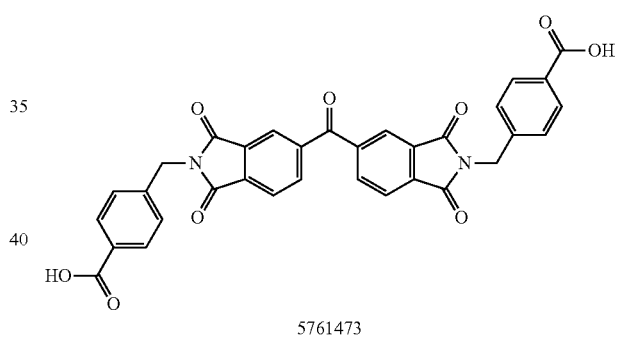

5761473

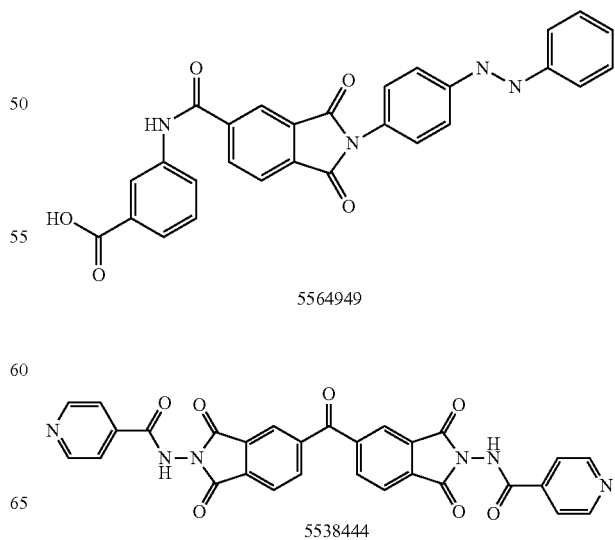

5564949

5538444

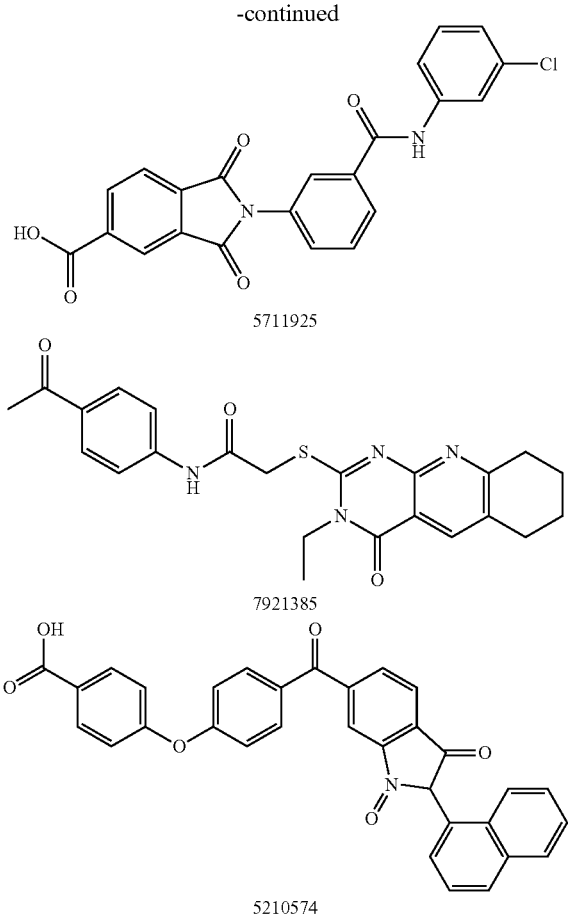

5711925

7921385

5210574

As alluded to above, these compounds were determined through docking studies which additionally provided insight into unforeseen binding modes. The 7839888 compound was selected for in silico evaluation on the basis of the oxocarboxylate functional group, which was expected to interact favorably with the active site metal ions. The thiourea functional group of this compound was found to involve in ligating one of the active site metal ions. This interaction and the electrostatic interactions of the carboxylate functional group with 8284 and K249 are likely responsible for the resultant 59% ATX inhibition observed. The other compounds were found to meet the desired ATX inhibition levels as well, as provided in the Examples below.

Previously reported ATX inhibitors are all analogs of the catalytic product, LPA, and fail to meet most metrics applied to determine drug-likeness. The most common of these metrics are Lipinski's rules. These rules are based on the observation that poor biological distribution occurs when solubility and permeability are reduced due to excessive molecular weight ($\geq 500$), large numbers of hydrogen bond donors or acceptors ($\geq 5$ or $\geq 10$, respectively), and calculated log P ($\geq 5$). Several extensions to Lipinski's rules have appeared in the literature. It has been found that increasing flexibility as reflected in an increasing number of rotatable bonds reduces oral bioavailability. Nine compounds were identified in the current study as reducing the ATX-catalyzed FS-3 hydrolysis by 50% or more at 10 μM. Two of these compounds (5711925 and 7921385, presented above) comply with all of Lipinski's rules and have fewer than 10 rotatable bonds, thus also meeting the extended flexibility metric. Five additional compounds (7839888, 5186522, 5761473, 5538444 and 7905958, above) exceed only the molecular weight limit by amounts ranging from 7 (7905958) to 148 (5186522). One compound (5564949) exceeds only the calculated log P criterion. The final compound (5210574) exceeds two criteria, calculated log P and molecular weight. None of the compounds violated the recommended limits on rotatable bonds, hydrogen bond acceptors, or hydrogen bond donors. Thus the goal of demonstrating that ATX is a 'druggable' target has been achieved in terms of these nine compounds, at least exhibited the necessary results under Lipinski's rules coupled with effective ATX inhibition (as presented in the Examples, below).

As such, these compounds may be included in a composition of any type that is properly ingestable by a patient. It is preferable that such compositions be orally ingestable, but they may be provided for intravenous introduction as well.

In terms of the form such compositions may take, any orally ingestable form is possible. This list includes, without limitation, liquids, liquid capsules, tablets, coated tablets, minitablets, capsules with individual beads, and the like. If in coated tablet form, such compositions may be of sustained release type, and may include a water insoluble but permeable film coating surrounding a core tablet and a particulate, water-soluble, pore-forming material dispersed within the film coating. Such a system thus provides an osmotic gradient and channel forming system. Typical coatings have included carnauba wax, cysteine hydrochloride, hydroxypropyl methylcellulose, magnesium stearate, microcrystalline cellulose, polyethylene glycol and titanium dioxide. Other therapeutic agents may be included with these anticancer agents as well, as long as neither interferes with the effectiveness of the other in the user's body.

Preferred Embodiments of the Invention

The specific compounds below, as well as the following exemplified methods of producing such and methods of using such compounds are non-limiting in nature and are thus indicative of the preferred embodiments of this invention.

The efficacy of these compounds was determined by evaluating fluorescence of autotaxin at specific wavelengths. The test protocol was as follows:

In terms of ATX inhibition analysis determinations, MDA-MB-435 cells were cultured at 37° C. and 5% $CO_2$ in Dulbecco's Modified Eagle Medium (DMEM) (MediaTech, Herndon, Va.) containing 5% fetal bovine serum (Hyclone, Logan, Utah), 100 U/ml penicillin, 100 μg/ml streptomycin (Hyclone, Logan, Utah) and 292 μg/ml L-glutamine (Hyclone, Logan, Utah). Cells were grown to ~80% confluence at which time the cells were washed twice with sterile phosphate buffered saline prior to the addition of serum free DMEM containing L-glutamine. Conditioned medium was collected after 24-30 hours, supplemented with 20% ethylene glycol and was clarified by centrifugation at 3000×g and 4° C. for 10 min. The media was concentrated ~10 fold and buffer exchanged into Tris (50 mM, pH 7.4) containing 20% ethylene glycol using an Amicon 8050 cell fitted with a PM30 filter (Millipore, Billerica, Mass.). Aliquots of concentrated conditioned media were stored at 4° C. until needed.

ATX inhibition was assayed using FS-3 (Echelon Biosciences, Inc., Salt Lake City, Utah, USA) as a substrate and ~10 times concentrated conditioned serum-free medium (CCM) from MDA MB-435 cells as the source of ATX. Assays were performed in 96-well plates with CCM comprising one-third of the total volume and final FS-3 and charcoal-stripped fatty acid free BSA concentrations of 1 and 30 μM in assay buffer (1 mM each $CaCl_2$ and $MgCl_2$, 5 mM KCl, 140 mM NaCl, 50 mM Tris pH 8.0). Fluorescence was read at 5 minute intervals by a Synergy2 system (BioTek, Winooski, Vt.) with excitation and emission wavelengths of 485 and 538 nm, respectively. Results are shown at 1 hour, at which point all fluorescence changes as a function of time were linear. Fluorescence readings were normalized to vehicle control after subtraction of fluorescence in the absence of CCM. Data are shown as the mean±S.D. of at least three wells.

Each of the nine compounds determined for effective ATX inhibition through the modeling method delineated above were purchased from ChemBridge under the numbers assigned above and herein.

TABLE 1 provides the ATX activity reductions (at 10 micromole concentrations) for these assays.

TABLE 1

| ATX Inhibition | |
|---|---|
| Compound ID # | % ATX Activity at 10 μM |
| 7839888 | 41 ± 9 |
| 5564949 | 45 ± 10 |
| 5711925 | 48 ± 5 |
| 5186522 | 49 ± 10 |
| 5761473 | 46 ± 6 |
| 5538444 | 31 ± 4 |
| 7921385 | 21 ± 6 |
| 5210574 | 31 ± 5 |
| 7905958 | 0 ± 4 |

Thus, it is evident that the inventive compounds exhibit excellent potential for autotaxin inactivation, particularly the 7905958 compound with essentially no ATX activity detected at all. Coupled, again, with the oral bioavailability results noted above, these compounds who great promise in providing orally ingestable tumor treatments for certain cancers.

There are, of course, many alternative embodiments and modifications of the present invention which are intended to be included within the spirit and scope of this invention.

We claim:

1. A method for inhibiting autotaxin activity through the reaction of autotaxin with at least one thiourea compound wherein said thiourea compound exhibits a molecular weight of at most 527, wherein said thiourea compound includes a terminal carboxylate group; wherein said thiourea compound meets all extended flexibility metrics of Lipinski's rules for biological distribution; and wherein said thiourea compound exhibits an autotaxin inhibition capability of at least 59% through a reduction in available reaction sites thereon to prevent autotaxin conversion of lysophosphatidyl choline to lysophosphatidic acid, wherein said autotaxin inhibition capability involves ligation of autotaxin active site metal ions through the thiourea functional group, as well as the simultaneous electrostatic interactions of said terminal carboxylate group with autotaxin constituent proteins.

2. The method of claim 1 wherein said at least one thiourea compound is selected from the group consisting of:

Compound 7905958

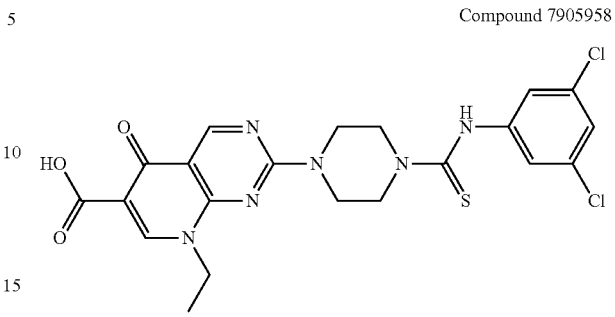

Compound 7839888

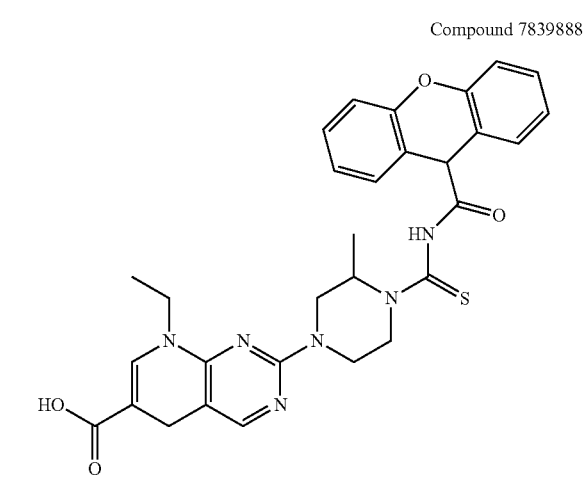

Compound 7921385

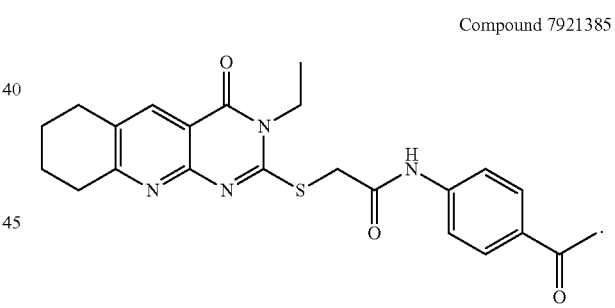

3. The method of claim 1 wherein said at least one thiourea compound exhibits an autotaxin inhibition capability of at least about 79%.

4. The method of claim 1 wherein said at least one thiourea compound exhibits an autotaxin inhibition capability of about 100%.

* * * * *